United States Patent [19]

Sakai et al.

[11] Patent Number: 4,503,068

[45] Date of Patent: Mar. 5, 1985

[54] USE OF PROSTAGLANDIN ANALOGUES TO TREAT CYTODAMAGE

[75] Inventors: Yoshiki Sakai, Mishimagun; Katsuhiro Imaki, Tsuzukigun; Takashi Muryobayashi, Takatsuki, all of Japan

[73] Assignee: Ono Pharmaceutical Co., Ltd., Osaka, Japan

[21] Appl. No.: 497,052

[22] Filed: May 23, 1983

[30] Foreign Application Priority Data

May 25, 1982 [JP] Japan .................. 57-87230

[51] Int. Cl.$^3$ .................. A61K 31/40; A61K 31/34; A61K 31/19
[52] U.S. Cl. .................. 514/412; 514/469; 514/530; 514/573
[58] Field of Search .............. 424/285, 274, 305, 317

[56] References Cited

U.S. PATENT DOCUMENTS 4,178,367 12/1979 Masaki et al. .
4,313,954 2/1982 Wakatsuka .

Primary Examiner—Sam Rosen

Attorney, Agent, or Firm—Stevens, Davis, Miller & Mosher

[57] ABSTRACT

The prostaglandin analogues
16S-methyl-6-oxo-$PGE_1$ methyl ester,
17S,20-dimethyl-6-oxo-$PGE_1$ methyl ester,
15S-methyl-6-oxo-$PGE_1$ and non-toxic salts thereof,
17S,20-dimethyl-13,14-dihydro-6-oxo-$PGE_1$ methyl ester,
17S,20-dimethyl-6-oxo-$PGE_1$ alcohol,
17S,20-dimethyl-6S-$PGI_1$ methyl ester,
17S,20-dimethyl-trans-$\Delta^2$-6RS-$PGI_1$ methyl ester,
17S,20-dimethyl-6,9α-nitrilo-$PGI_1$ methyl ester,
2-decarboxy-2-glycoloyl-17S,20-dimethyl-6S-$PGI_1$,
2-decarboxy-2-glycoloyl-15-cyclopentyl-16,17,18,19,20-pentanor-6S-$PGI_1$,
17S,20-dimethyl-6S-$PGI_1$ alcohol,
15-cyclopentyl-16,17,18,19,20-pentanor-6S-$PGI_1$ alcohol and
15-(3-propylcyclopentyl)-16,17,18,19,20-pentanor-6,9α-nitrilo-$PGI_1$ alcohol, and cyclodextrin clathrates thereof are useful in the prevention or treatment of cytodamage.

17 Claims, No Drawings

USE OF PROSTAGLANDIN ANALOGUES TO TREAT CYTODAMAGE

DESCRIPTION

This invention relates to a new use of prostaglandin analogues, in the treatment of disease caused by cytodamage.

Prostaglandins are derivatives of prostanoic acid which has the following formula:

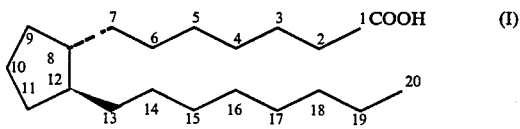

Various types of prostaglandins are known, the types depending inter alia on the structure and substituents on the alicyclic ring. For example, the alicyclic ring of prostaglandin E(PGE) has the structure:

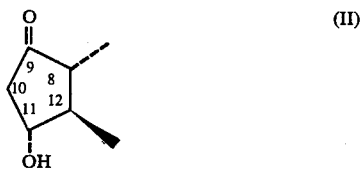

The dotted lines in the foregoing formulae and in other formulae throughout this specification denote, in accordance with generally accepted rules of nomenclature, that the attached grouping lies behind the general plane of the ring system, i.e. that the grouping is in α-configuration, and the thickened lines denote that the grouping lies in front of the general plane of the system, i.e. that the grouping is in β-configuration. The wavy line in other formulae throughout this specification indicates that the grouping is in α- or β-configuration or a mixture thereof.

Such compounds are sub-classified according to the position of double bond(s) in the side chain(s) attached to the 8- and 12-positions of the alicyclic ring. $PG_1$ compounds have a trans-double bond between $C_{13}$–$C_{14}$ (trans-$\Delta^{13}$). Prostaglandin $E_1$ ($PGE_1$) is characterised by the following structure (III):

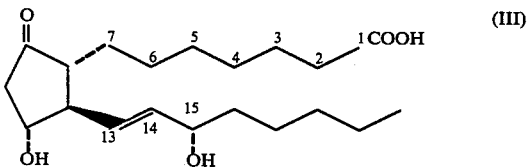

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di- tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGE's have a stimulating effect on smooth muscle and increase the intestinal peristalsis; these actions indicate therapeutic utility on post-operative ileus and as purgatives. PGE's may also be used as oxytocics, as abortifacients in the first and second trimesters; in the post-labour abortion of the placenta, and as oral contraceptives because they regulate the sexual cycle of female mammals. PGE's have vasodilator and diuretic activities. They are useful for improvement in patients suffering from cerebral vascular disease because they increase the cerebral blood flow, and are also useful in the treatment of asthmatic conditions in patients because of their bronchodilating activity.

$PGI_2$ is a physiologically active substance having the following formula:

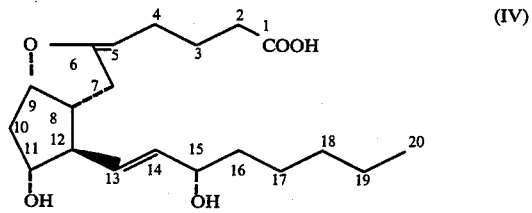

and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that $PGI_2$ can be prepared by incubation of prostaglandin $G_2$ ($PGG_2$) or prostaglandin $H_2$ ($PGH_2$) with microsomal fractions prepared from thoracic aorta of swine, mesenteric artery of swine, rabbit aorta or the stomach fundus of rats. $PGI_2$ has a relaxing activity on the artery, which is peculiar to the artery and which does not operate on other smooth muscle. Furthermore, $PGI_2$ strongly inhibits arachidonic acid-induced blood platelet aggregation of the human.

Taking into consideration that thromboxane $A_2$ prepared by incubation of $PGG_2$ or $PGH_2$ with blood platelet microsome, has a contracting activity on the artery and an aggregating activity on blood platelets, the properties of $PGI_2$ heretofore mentioned show that $PGI_2$ fulfils a very important physiological part in a living body. $PGI_2$ may be useful in the treatment of arteriosclerosis, cardiac failure or thrombosis.

Recently, it has been found that certain individual prostaglandin analogues have a previously unknown activity. This activity is to protect cells in the living body.

For example, it was reported by T. Manabe et al that $PGE_2$ was effective against a diet-induced acute pancreatitis in mice [cf. Gastroenterology, 78, 777–781 (1980)]. It was reported by J. Stachura et al that 16,16-dimethyl-$PGE_2$ prevents acute galactosamine-induced liver damage and carbon tetrachloride-induced liver cell necrosis [cf. Folia Histochemica et Cytochemica, 18, 311–318(1980) and Gastroenterology, 81, 211–217 (1981), respectively]. Further, it was reported that $PGI_2$ prevents and is useful in treating hypoxia in the isolate perfused cat liver, endotoxin shock in dog, ischemic myocardial tissue in cat and endotoxin-induced lung injury in sheep [cf. H. Araki et al, Am. J. Physiol., 238, H176-H181 (1980), J. R. Fletcher et al, Circulatory Shock, 7, 299–308 (1980), H. Araki et al, Circulation Research, 47, No. 5, 757–763 (1980) and R. H. Demling et al, Surgery, 89, No. 2, 257–263 (1981), respectively].

Although the mechanism of the new activity is not yet clear, the activity is collectively named cytoprotective activity. It will be apparent from the above reports, that only a small number of individual prostaglandins or prostaglandin analogues have been found to have cytoprotective activity.

As a result of research and investigation it has been found that only a very limited number of, and not all, prostaglandin analogues have cytoprotective activity. In particular, it has surprisingly been discovered that certain prostaglandin compounds in which the n-pentyl group attached to the 15-position of the prostaglandin skeleton is replaced by a cyclopentyl or 3-propylcyclopentyl group and certain prostaglandin compounds in which hydrogen attached to the 15- or 16-position or 17- and 20-positions of the prostaglandin skeleton is replaced by methyl, have strong cytoprotective activity.

The present invention accordingly provides a method for the treatment (which may be preventive treatment) of cytodamage in a mammalian host, which comprises administering to a host suffering from, or subject to, cytodamage at least one prostaglandin analogue selected from the group consisting of 16S-methyl-6-oxo-$PGE_1$ methyl ester,
17S,20-dimethyl-6-oxo-$PGE_1$ methyl ester,
15S-methyl-6-oxo-$PGE_1$,
17S,20-dimethyl-13,14-dihydro-6-oxo-$PGE_1$ methyl ester,
17S,20-dimethyl-6-oxo-$PGE_1$ alcohol,
17S,20-dimethyl-6S-$PGI_1$ methyl ester,
17S,20-dimethyl-trans-$\Delta^2$-6RS-$PGI_1$ methyl ester,
17S,20-dimethyl-6,9α-nitrilo-$PGI_1$ methyl ester,
2-decarboxy-2-glycoloyl-17S,20-dimethyl-6S-$PGI_1$,
2-decarboxy-2-glycolyl-15-cyclopentyl-16,17,18,19,20-pentanor-6S-$PGI_1$,
17S,20-dimethyl-6S-$PGI_1$ alcohol,
15-cyclopentyl-16,17,18,19,20-pentanor-6S-$PGI_1$ alcohol and
15-(3-propylcyclopentyl)-16,17,18,19,20-pentanor-6,9α-nitrilo-$PGI_1$ alcohol,
or a cyclodextrin clathrate thereof,
or a non-toxic salt of 15S-methyl-6-oxo-$PGE_1$.

16S-Methyl-6-oxo-$PGE_1$ methyl ester, 17S,20-dimethyl-6-oxo-$PGE_1$ methyl ester, 15S-methyl-6-oxo-$PGE_1$, 17S,20-dimethyl-13,14-dihydro-6-oxo-$PGE_1$ methyl ester and 17S,20-dimethyl-6-oxo-$PGE_1$ alcohol are compounds represented by the formulae shown below, respectively:

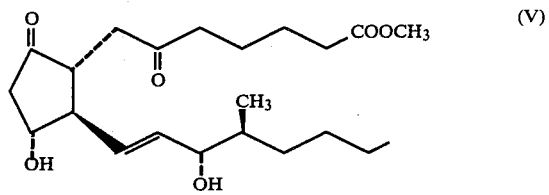

(V)

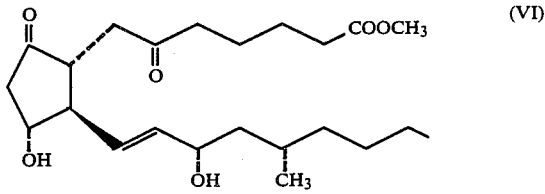

(VI)

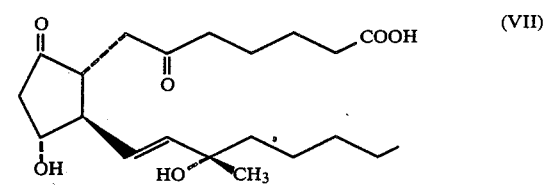

(VII)

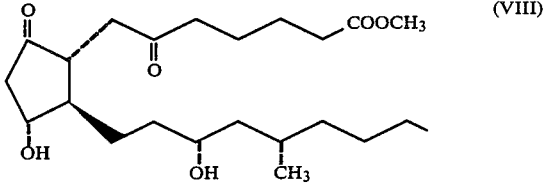

(VIII)

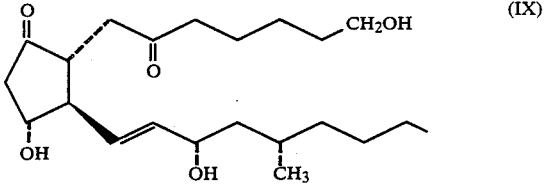

(IX)

The compounds represented by the formulae from (V) to (VIII) and a process for their preparation are described in detail in the specification of U.S. Pat. No. 4,215,142. The compound represented by the formula (IX) may be prepared by the series of reactions shown in Scheme A. (In Scheme A "DIBAL" is diisobutylaluminium hydride).

Scheme A

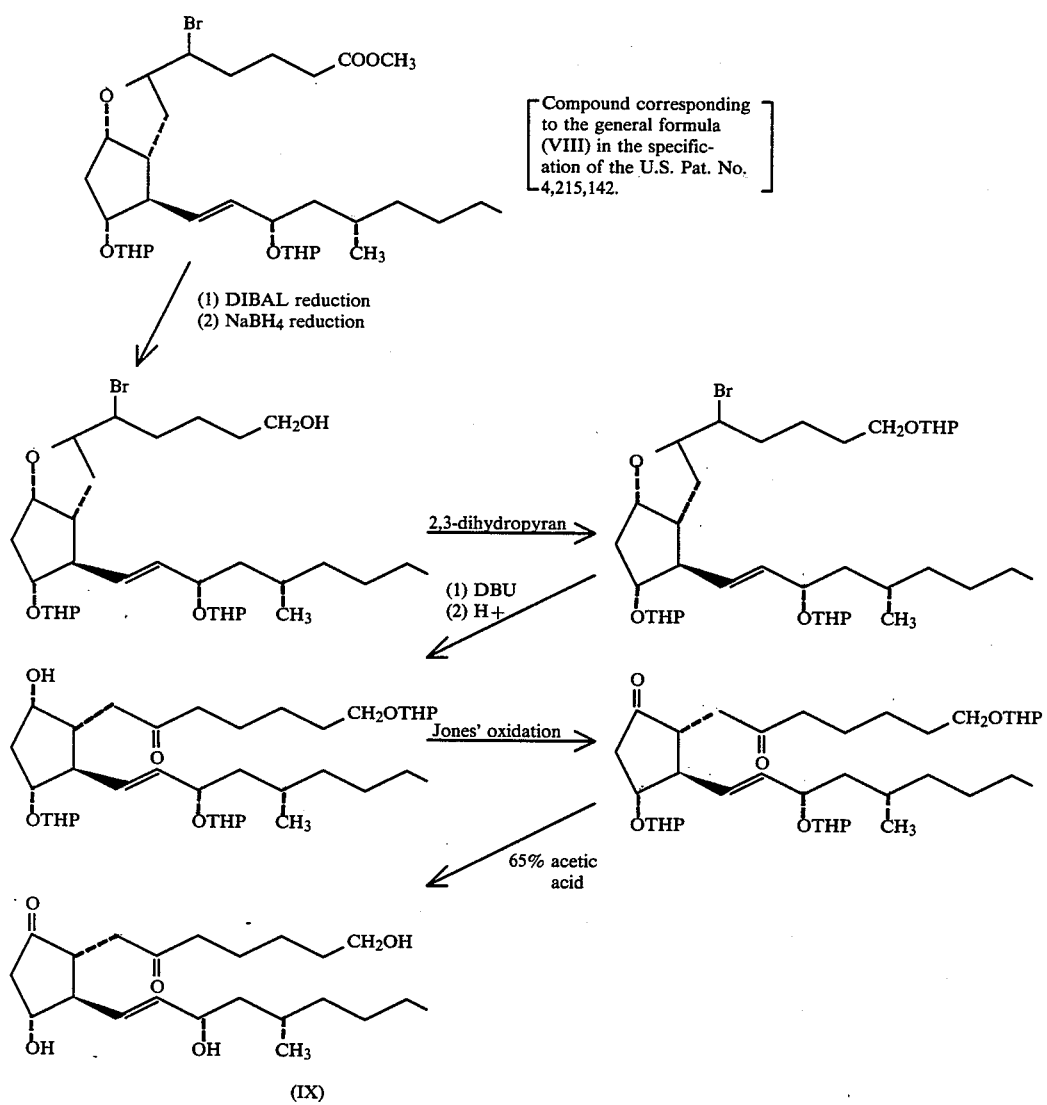

17S,20-Dimethyl-6S-PGI$_1$ methyl ester and 17S,20-dimethyl-trans-$\Delta^2$-6RS-PGI$_1$ methyl ester are compounds represented by the formulae shown below, respectively:

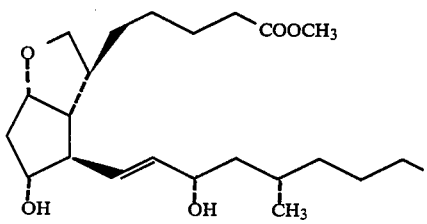

The compound represented by formula (X) and a process for its preparation is described in detail in the specification of W. German Patent publication No. 2,803,638. The compound represented by formula (XI) may be prepared from the compound represented by formula (II) in the specification of W. German Patent Publication No. 2,803,638, with the introduction of a trans-vinylene group, by the method described in the specification of Japanese Patent Publication No. 53-137952.

17S,20-Dimethyl-6,9α-nitrilo-PGI₁ methyl ester is a compound represented by the formula shown below:

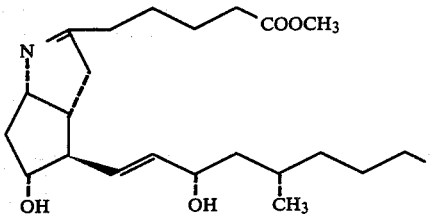
(XII)

The compound represented by formula (XII) and a process for its preparation is described in detail in the specification of U.S. Pat. No. 4,313,954.

2-Decarboxy-2-glycoloyl-17S,20-dimethyl-6S-PGI₁ and 2-decarboxy-2-glycoloyl-15-cyclopentyl-16,17,18,19,20-pentanor-6S-PGI₁ are compounds represented by the formulae shown below, respectively:

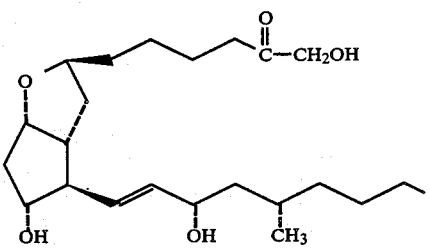
(XIII)

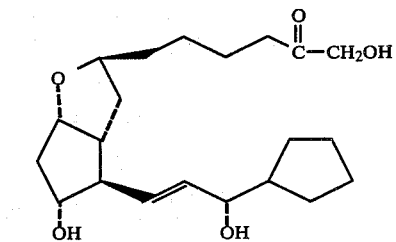
(XIV)

The compounds represented by formulae (XIII) and (XIV) may be prepared by the series of the reactions shown in the next Scheme B.

Scheme B

[Compounds corresponding to the general formula (III) in the specification of the U.S. Pat. No. 4,178,367. R in the formulae represents a 2-methylhexyl or cyclopentyl group.]

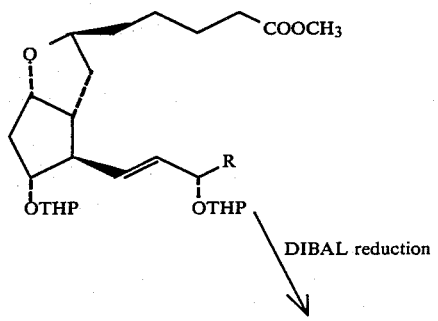

DIBAL reduction

-continued
Scheme B

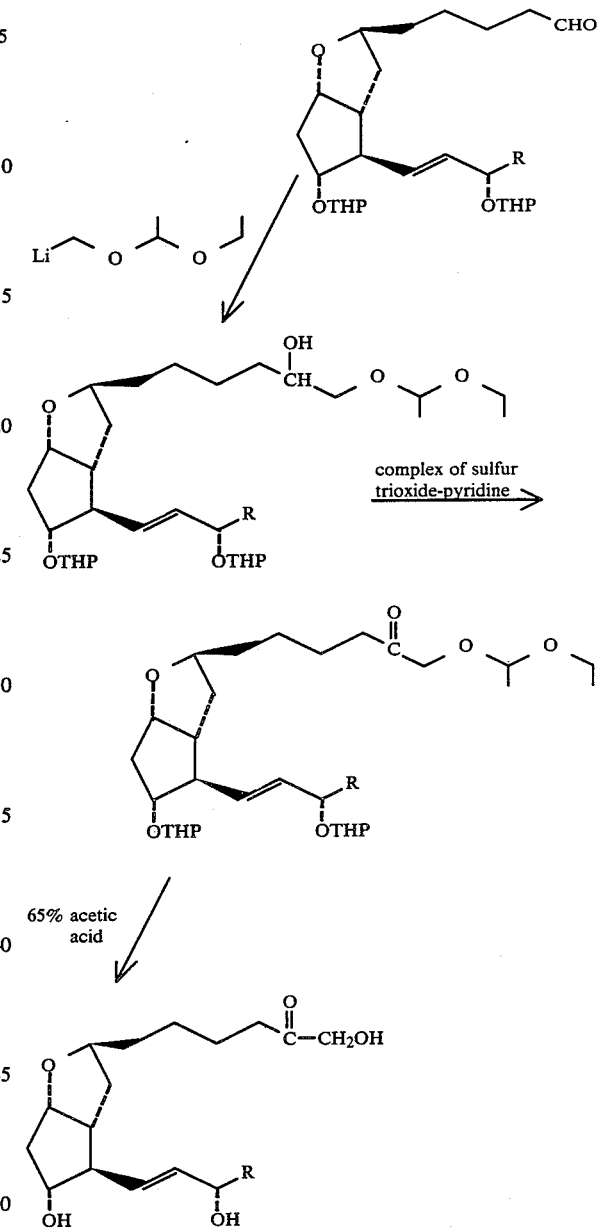

complex of sulfur trioxide-pyridine

65% acetic acid 17S,20-Dimethyl-6S-PGI₁ alcohol and 15-cyclopentyl-16,17,18,19,20-pentanor-6S-PGI₁ alcohol are compounds represented by the formulae shown below, respectively:

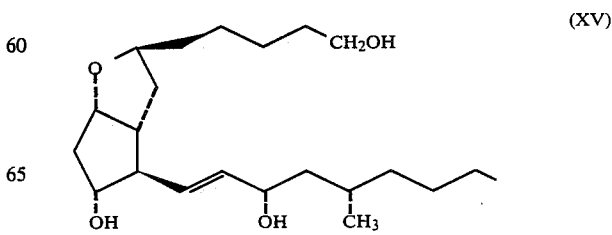
(XV)

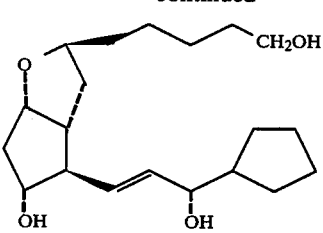
(XVI)

The compounds represented by formulae (XV) and (XVI) may be prepared from the corresponding alkyl esters of the prostaglandin analogues which are prepared by the process described in the specification of the U.S. Pat. No. 4,178,367, by reduction with diisobutylaluminium hydride (DIBAL).

15-(3-Propylcyclopentyl)-16,17,18,19,20-pentanor-6,9α-nitrilo-PGI$_1$ alcohol is a compound represented by the formula shown below:

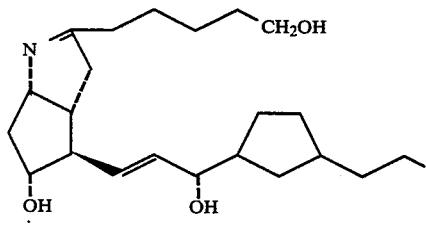
(XVII)

The compound represented by formula (XVII) may be prepared by the series of reactions shown in the Scheme C.

Scheme C

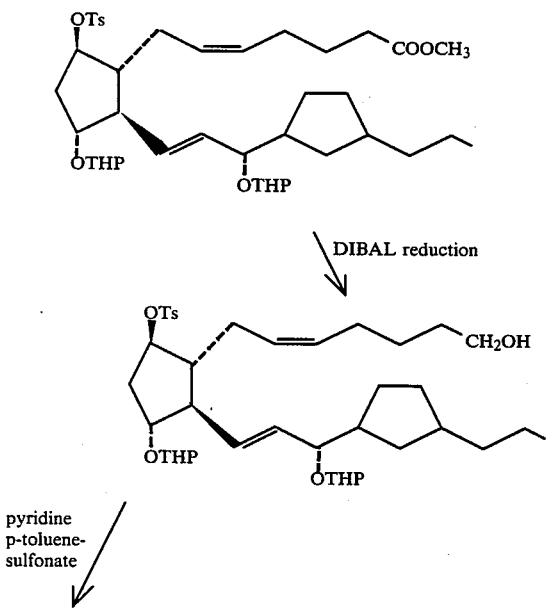

-continued
Scheme C

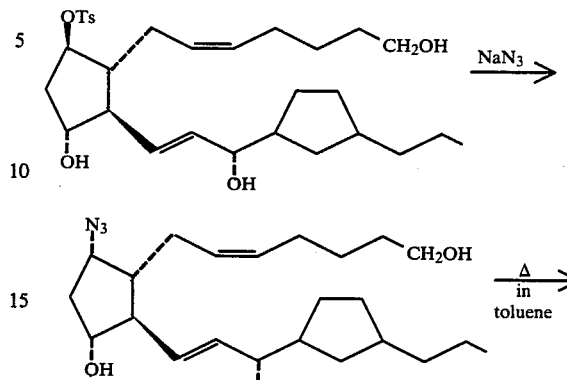

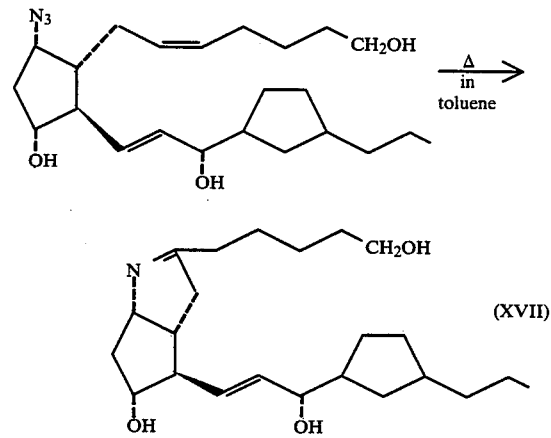
(XVII)

Although certain of the prostaglandin analogues used in the method of the invention are known per se, the fact that they have cytoprotective activity was heretofore unknown and there is no disclosure of such activity in the patent specifications referred to above.

Especially preferred prostaglandin analogues for use in the method of the invention are:
16S-methyl-6-oxo-PGE$_1$ methyl ester,
17S,20-dimethyl-6-oxo-PGE$_1$ methyl ester,
17S,20-dimethyl-13,14-dihydro-6-oxo-PGE$_1$ methyl ester,
17S,20-dimethyl-6-oxo-PGE$_1$ alcohol,
17S,20-dimethyl-6S-PGI$_1$ methyl ester,
17S,20-dimethyl-trans-Δ$^2$-6RS-PGI$_1$ methyl ester,
17S,20-dimethyl-6,9α-nitrilo-PGI$_1$ methyl ester,
2-decarboxy-2-glycoloyl-17S,20-dimethyl-6S-PGI$_1$,
17S,20-dimethyl-6S-PGI$_1$ alcohol and
15-(3-propylcyclopentyl)-16,17,18,19,20-pentanor-6,9α-nitrilo-PGI$_1$ alcohol,
and cyclodextrin clathrates thereof.

The compounds of formulae (V) to (XVII), and cyclodextrin clathrates thereof, and non-toxic salts of the compound of formula VII, possess strong cytoprotective activity and have low toxicity, as demonstrated by results given hereinafter. They may therefore be used in the treatment (including preventive treatment) of diseases associated with cell damage, especially liver damage. Their cytoprotective activity and low toxicity indicates utility in the treatment of many diseases as follows:

(1) digestive system diseases associated with cytodamage, for example:

(i) liver diseases such as acute yellow atrophy, fatty liver (especially of the alcoholic type), hepatic coma, hepatitis (especially of the alcoholic type, toxic type, hepatitis A or hepatitis B), hepatolenticular disease, hepatomegaly, portal hypertension, obstructive jaundice (especially cholestasis), liver abscess, liver cirrhosis (especially of the alcoholic type and biliary type), parasitic liver diseases, liver neoplasms and hepatic tuberculosis;

(ii) pancreatic diseases such as pancreatitis; and (iii) diseases of other digestive systems, eg biliary tract diseases such as biliary dyskinesia, cholangitis, oesophagal diseases, intestinal diseases such as enteritis, ileitis and proctitis, and stomach diseases.

It has been reported that the results of liver function tests which are extensively used in clinics correlate fully with the findings of liver histological examination and liver cell damage, ie the degree of degeneration, necrosis and inflammation is accurately reflected in plasma glutamic oxaloacetic transaminase (GOT) and plasma glutamic pyruvic transaminase (GPT) levels. It is considered that drugs which suppress GOT and GPT activities in the experimental liver damage models described hereinafter are also effective in preventing or treating human liver damage, and in preventing or treating cell damage associated with other diseases and ailments.

The compounds of the formulae from (V) to (XVII) will generally be used in the form of pharmaceutical compositions which comprise a compound of formulae from (V) to (XVII), or cyclodextrin clathrate thereof, or non-toxic salt of the compound of formula VII, together with a pharmaceutical carrier or coating.

In clinical practice, for the treatment of cytodamage, the compounds of formulae (V) to (XVII), or cyclodextrin clathrate thereof, or non-toxic salt of the compound of formula VII, will normally be administered systemically or partially; usually by oral or parenteral (e.g. intravenous, subcutaneous or intramuscular) administration.

Solid compositions for oral administration include compressed tablets, pills, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, and disintegrating agents, such as cellulose calcium gluconate. The tablets or pills may, if desired, be made into enteric film-coated or gastric film-coated tablets or pills, such as sugar-coated, gelatin-coated, hydroxypropylcellulose-coated or hydroxypropylmethylcellulose phthalate-coated tablets or pills; two or more layers may be used.

The compositions for oral administration also include capsules of absorbable material such as gelatin, containing one or more of the active substances with or without the addition of diluents or excipients.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise at least one compound of the present invention.

Preparations for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark).

These compositions may also include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions include, for parenteral administration, liquids for external use, and endermic liniments such as ointments; suppositories for rectal administration; and pessaries for vaginal administration. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, symptoms, the desired therapeutic effects, the route of administration, and the duration of the treatment.

In the human adult, the doses per person are generally between 0.1 and 100 $\mu g$, preferably between 1 and 50 $\mu g$ by oral administration, and between 0.01 and 50 $\mu g$, preferably between 0.1 and 20 $\mu g$ by parenteral administration in the prevention or treatment of cytodamage, and can be administered up to several times per day. In particular the doses are preferably administered 3 or 4 times per day at a total daily dose of 0.4–400 $\mu g$ per day, in the prevention or treatment of cyto-damage.

In domestic mammals, such as cows, mares, sows, ewes and bitches, the doses are generally between 0.1 and 100 82 g per kg, preferably between 1 and 50 $\mu g$ per kg by oral administration, and between 0.01 and 10 $\mu g$ per kg, preferably 0.1 and 5 $\mu g$ per kg, by parenteral administration in the treatment or prevention of cytodamage, and can be administered 3 or 4 times per day.

As mentioned above, the doses to be used depend on various factors. Therefore, there may be cases in which doses greater than the ranges specified above, or lower than the ranges specified above, may be used.

The following Experiments and Examples illustrate biological activities and the preparation of pharmaceutical compositions of the compounds of this invention.

EXPERIMENT 1

Effect on carbon tetrachloride ($CCl_4$) induced liver damage (liver cell necrosis type)

Male Wistar rats weighing 180–220 g were used. Rats were dosed intraperitoneally with $CCl_4$ dissolved in olive oil (5% w/v) at a volume of 500 $\mu l/kg$ after 18 hr starvation. The compound under test was administered orally (p.o.) or subcutaneously (s.c.) 6 and 12 hr after $CCl_4$ injection in rats and blood was collected after 24 hr. Plasma glutamic oxaloacetic transaminase (GOT) and glutamic pyruvic transaminase (GPT) activities were determined by ultraviolet absorbance methods (optimised method based on the recommendations of the Deutsche Gesellschaft für Klinische Chemie). The effects of the compounds tested were assessed by the inhibition rate in comparison with controls. Inhibition rate was calculated by the following formula.

$$\text{Inhibition (\%)} = \left(1 - \frac{\text{treated value}}{\text{control value}}\right) \times 100$$

The results obtained are shown in the following Table 1.

In Tables 1 to 4 hereinafter the dose shown is the amount given at each administration of the compound under test.

TABLE 1

| compound No. | route of administration | dose (μg/kg) | inhibition rate (%) GOT | GPT |
|---|---|---|---|---|
| 1. | p.o. | 100 | 59.9 | 53.5 |
|    | s.c. | 20 | 27.8 | 16.3 |
| 2. | p.o. | 50 | 61.5 | 44.1 |
|    | s.c. | 20 | 37.9 | 34.6 |
| 3. | p.o. | 100 | 6.8 | 13.2 |
| 4. | p.o. | 100 | 52.1 | 62.3 |
| 5. | p.o. | 50 | 56.6 | 59.1 |
| 6. | s.c. | 500 | 55.3 | 64.6 |
| 7. | p.o. | 1000 | 58.0 | 42.7 |
| 8. | p.o. | 1000 | 41.1 | 14.5 |
|    | s.c. | 500 | 65.6 | 58.6 |
| 9. | s.c. | 500 | 58.4 | 51.4 |
| 10. | s.c. | 1000 | 11.8 | 0 |
| 11. | s.c. | 500 | 73.3 | 65.2 |
| 12. | p.o. | 2000 | 7.4 | 44.1 |
| 13. | p.o. | 1000 | 53.6 | 58.2 |

Names and physical characteristics of the compounds used in Experiment 1 are described in the following. In the physical characteristics, 'TLC', 'IR', 'NMR' and 'Mass' represent 'Thin layer chromatography', 'Infrared absorption spectrum', 'Nuclear magnetic resonance' and 'Mass spectrum', respectively. Where solvent ratios are specified in chromatographic separations, the ratios are by volume: the solvents in parentheses in thin layer chromatography show the developing solvents used. Except when specified otherwise, infrared spectra are recorded by the liquid film method and nuclear magnetic resonance spectra are recorded in deuterochloroform ($CDCl_3$) solution.

The less polar isomer of the compound represented by the formula (XVII) was tested as compound No. 13.

Compound No. 1 [formula (V)]: 16S-methyl-6-oxo-$PGE_1$ methyl ester (Physical characteristics of this compound were described in Example 2(a) of the specification of the U.S. Pat. No. 4,215,142).

Compound No. 2 [formula VI)]: 17S,20-dimethyl-6-oxo-$PGE_1$ methyl ester (Physical characteristics of this compound were described in Example 2(f) of the specification of the U.S. Pat. No. 4,215,142).

Compound No. 3 [formula VII)]: 15S-methyl-6-oxo-$PGE_1$

TLC(chloroform:tetrahydrofuran:acetic acid=10:2:1): Rf=0.19;
IR:$\nu$=3410,2950,1745,1710,1380,1250,1090,980 $cm^{-1}$;
NMR:$\delta$=6.4~5.35(5H,m), 4.4~3.85(1H,m), 0.88(3H,t);
Mass:m/e=364($M^+$-18), 346, 293, 217, 202, 129, 111, 55.

Compound No. 4 [formula (VIII)]: 17S,20-dimethyl-13,14-dihydro-6-oxo-$PGE_1$ methyl ester
TLC (ethyl acetate): Rf=0.56;
IR: $\nu$=3400, 1740, 1720, 1380, 1160 $cm^{-1}$;
NMR: $\delta$=4.20~4.08(1H,m),3.80~3.68(1H,m), 3.68(3H,s),2.86~2.68(3H,m), 2.54~2.22(6H,m), 0.98~0.84(6H,m);
Mass; m/e=412($M^+$), 394, 381, 376, 363.

Compound No. 5 [formula (IX)]: 17S,20-dimethyl-6-oxo-$PGE_1$ alcohol
TLC (ethyl acetate): Rf=0.13;
IR: $\nu$=3350, 2925, 1740, 1710, 1455, 1400 $cm^{-1}$;
NMR: $\delta$=5.72~5.41(2H,m),4.22~4.00(2H,m), 3.71~3.56(2H,t),2.88~2.64(3H,m), 2.58~2.26(6H,m),1.74~1.05(15H,m), 1.00~0.81(6H,m);
Mass: m/e=382($M^+$), 364, 346, 328, 265, 247, 219, 209, 133, 115, 97, 69.

Compound No. 6 [formula (X)]: 17S,20-dimethyl-6S-$PGI_1$ methyl ester
TLC (ethyl acetate): Rf=0.25;
IR: $\nu$=3380, 1736, 978 $cm^{-1}$;
NMR: $\delta$=5.52(2H,m),4.43(1H,q)4.15(1H,m), 3.95(1H,m),3.68(1H,m),3.67(3H,s), 2.6~2.2(7H,m),2.03(1H,m), 0.89(6H,m);
Mass: m/e=378($M^+$-18),365, 360, 347, 334, 306.

Compound No. 7 [formula (XI)]: 17S,20-dimethyl-trans-$\Delta^2$-6RS-$PGI_1$ methyl ester
TLC (ethyl acetate): Rf=0.35;
IR: $\nu$=3370, 1725, 1655, 1440, 970 $cm^{-1}$;
NMR: $\delta$=6.99(1H,dt),5.84(1H,d),5.51(2H,m), 4.43(1H,m), 4.25~3.55(3H,m), 3.72(3H,s), 0.90(6H,m).

Compound No. 8 [formula (XII)]: 17S,20-dimethyl-6,9α-nitrilo-$PGI_1$ methyl ester (Physical characteristics of this compound were described in Example 2 of the specification of the U.S. Pat. No. 4,313,954)

Compound No. 9 [formula (XIII)]: 2-decarboxy-2-glycoloyl-17S,20-dimethyl-6S-$PGI_1$
melting point: 76°–78° C.;
TLC (ethyl acetate:formic acid=400:5): Rf=0.08;
IR (KBr tablet method): $\nu$=3400,1726,1070,974 $cm^{-1}$;
NMR: $\delta$=5.55(2H,m),4.45(1H,q),4.24(2H,s), 4.17(1H,m),3.96(1H,m),3.71(1H,m), 0.9(6H,m);
Mass: m/e=378($M^+$-18), 365, 360, 347, 334, 306.

Compound No. 10 [formula (XIV)]: 2-decarboxy-2-glycoloyl-15-cyclopentyl-16,17,18,19,20-pentanor-6S-$PGI_1$
melting point: 89°–90° C.;
TLC (ethyl acetate:formic acid=400:5): Rf=0.09;
IR (KBr tablet method): $\nu$=3600~3200, 2950, 2860, 1720, 1420, 1370, 1320, 1295, 1080, 1060, 1020 $cm^{-1}$.
NMR: $\delta$=5.55(2H,m),4.43(1H,q),4.22(2H,s), 3.95(1H,m),3.85(1H,m),3.69(1H,m);
Mass: m/e=366($M^+$), 348, 335, 330, 304, 279, 276.

Compound No. 11 [formula (XV)]: 17S,20-dimethyl-6S-$PGI_1$ alcohol
TLC (ethyl acetate:formic acid=400:5): Rf=0.14;
IR: $\nu$=3340, 1050, 972 $cm^{-1}$;
NMR: $\delta$=5.55(2H,m),4.45(1H,m),4.17(1H,m), 3.97(1H,m),3.71(1H,m),3.64(2H,t), 2.38(2H,m),2.06(1H,m),0.9(6H,m);
mass: m/e=368($M^+$), 350, 332, 321, 306.

Compound No. 12 [formula (XVI)]: 15-cyclopentyl-16,17,18,19,20-pentanor-6S-PGI$_1$ alcohol
melting point: 67°–68° C.;
TLC (ethyl acetate): Rf=0.06;
IR (KBr tablet method): $\nu=3600\sim3100,2950,2850,1440,1340,1070$ cm$^{-1}$;
NMR: $\delta=5.65(2H,m),4.45(1H,q),3.95(1H,m),3.85(1H,dd),3.72(1H,dd),3.65(2H,t),2.38(2H,m),2.2\sim1.1(24H,m)$;
Mass: m/e=320, 302, 276, 251, 248.

Compound No. 13 [formula (XVII)]: 15-(3-propylcyclopentyl)-16,17,18,19,20-pentanor-6,9α-nitrilo-PGI$_1$ alcohol (less polar isomer)
TLC (ethyl acetate:methanol=9:1): Rf=0.06;
IR: $\nu=3300, 2930, 2850, 1635, 1440$ cm$^{-1}$;
NMR (methanol-d$_4$ solution): $\delta=5.53(2H,m),4.29(1H,m),3.88\sim3.63(2H,m),3.54(2H,t),2.88\sim2.26(4H,m),2.36(2H,t)$
$2.12\sim1.06(20H,m),0.90(3H,t)$;
Mass: m/e=377(M$^+$), 359, 348, 334, 318, 305, 266, 238, 236, 194, 166, 154, 94, 69.

EXPERIMENT 2

Effect on D(+)-galactosamine hydrochloride-induced liver damage (hepatitis type)

Male Wistar rats weighing 180–200 g were used. After the rats had fasted for 18 hr, 375 mg/kg galactosamine hydrochloride was administered to them intraperitoneally two times at 6 hr intervals. The compound under test was administered orally, 30 minutes before and, 6, 12 and 24 hr after the dose of D(+)-galactosamine hydrochloride and blood was collected after 24 and 48 hr. Plasma GOT and GPT activities were determined in the manner described in Experiment 1; plasma bilirubin activities were also determined. The effects were shown by the inhibition rate compared with controls (calculation by the formula shown in Experiment 1).

The results obtained are shown in Table 2.

TABLE 2

Effects on D(+)-galactosamine hydrochloride-induced liver damage

| Compound No. | route of administration | dose (μg/kg) | GOT 24 hr after | GOT 48 hr after | GPT 24 hr after | GPT 48 hr after | bilirubin 24 hr after | bilirubin 48 hr after |
|---|---|---|---|---|---|---|---|---|
| 2 | p.o. | 100 | 29.5 | 32.7 | 6.7 | 23.5 | 24.2 | 34.6 |
| 6 | p.o. | 2000 | 50.2 | 25.5 | 37.8 | 21.4 | 31.8 | 19.2 |
| 8 | p.o. | 1000 | 40.2 | 57.2 | 32.6 | 47.6 | 12.1 | 11.5 |

EXPERIMENT 3

Effect on α-naphthylisothiocyanate-induced liver damage (cholangioatresia type)

Male Wistar rats weighing 190–220 g were used. After rats had fasted for 18 hr, α-naphthylisothiocyanate (ANIT) dissolved in olive oil (1.5% w/v) was given orally to them at 30 mg/kg body weight. The compound under test was administered orally 30 min before and 6 and 12 hr after administration of ANIT and blood was collected after 24 hr. Plasma GOT, GPT and bilirubin activities were determined and the results given in Table 3 show the inhibition rate compared with controls (calculation by the formula shown in Experiment 1).

TABLE 3

Effects on α-naphthylisothiocyanate-induced liver damage (cholangioatresia type)

| Compound No. | route of administration | dose (μg/kg) | inhibition (%) GOT | inhibition (%) GPT | inhibition (%) bilirubin |
|---|---|---|---|---|---|
| 2 | p.o. | 100 | 39.6 | 41.9 | 37.5 |
| 5 | p.o. | 100 | 54.1 | 53.1 | 41.7 |
| 6 | p.o. | 2000 | 40.9 | 44.6 | 33.3 |
| 8 | p.o. | 1000 | 68.7 | 76.1 | 45.8 |

EXPERIMENT 4

Acute toxicity test

Male JCL-ICR mice (non SPF mice) from 7 weeks of age were used. The compound under test was dissolved in 5% v/v ethanol containing 0.4% w/v Tween 80 (Tween is a registered trademark) and administered orally to the mice. The mice were observed for 14 days. The calculated LD$_{50}$ values are shown in Table 4.

TABLE 4

| Compound No. | LD$_{50}$ (mg/kg) |
|---|---|
| 2 | 28–55 |
| 4 | >10 |
| 5 | >10 |
| 6 | >50 |
| 8 | 40–100 |
| 9 | >50 |
| 11 | >50 |

As shown in Table 4, the toxicity of the compounds of this invention, tested, is very low, i.e. the compounds are considered to be sufficiently safe and suitable for medical use.

The following Examples illustrate pharmaceutical compositions containing compounds of formula (V) to (XVII).

EXAMPLE 1

3 mg of 17S,20-dimethyl-6-oxo-PGE$_1$ methyl ester dissolved in 10 ml of ethanol, 100 mg of magnesium stearate, 20 mg of silicon dioxide, 10 mg of talc, 200 mg of cellulose calcium gluconate (CCG) and microcrystalline cellulose were mixed and dried in conventional manner. Sufficient microcrystalline cellulose was added to obtain 10 g of mixture. After mixing well, the mixture was punched out in conventional manner to obtain 100 tablets each containing 30 μg of the active ingredient.

EXAMPLE 2

To a mixture of 42 mg of α-cyclodextrin clathrate of 17S,20-dimethyl-6-oxo-PGE$_1$ methyl ester (content of the active ingredient was 3 mg), 100 mg of magnesium stearate, 20 mg of silicon dioxide, 10 mg of talc and 200 mg of CCG, microcrystalline cellulose was added to obtain 10 g of mixture. After mixing well, the mixture was punched out in conventional manner to obtain 100 tablets each containing 30 μg of the active ingredient.

EXAMPLE 3

To 42 mg of α-cyclodextrin clathrate of 17S,20-dimethyl-6-oxo-PGE$_1$ methyl ester (content of the active ingredient was 3 mg), lactose was added to obtain 21 g of mixture. After mixing well, the powder obtained was machine filled into 100 No. 3 gelatin capsules each containing 30 μg of the active ingredient.

EXAMPLE 4

A solution of 30 mg of 17S,20-dimethyl-6-oxo-PGE$_1$ methyl ester dissolved in 10 ml of chloroform was added to 100 ml of MCT (a mixture of triglycerides of fatty acids containing 8 to 10 carbon atoms) and the solution was mixed well. After removing chloroform under reduced pressure, the residue was machine filled into 1000 soft capsules each containing 30 μg of the active ingredient.

EXAMPLE 5

6 mg of α-cyclodextrin clathrate of 17S,20-dimethyl-6-oxo-PGE$_1$ methyl ester was dissolved in 300 ml of distilled water for injection. The solution was sterilized in conventional manner and placed in 3 ml portions in 5 ml ampoules to obtain 100 ampoules each containing 5 μg of the active ingredient.

We claim:

1. A method for the prevention or treatment of cytodamage associated with liver or pancreatic disease in a mammalian host which comprises administering to a host subject to, or suffering from, an aforesaid disease an effective amount of at least one prostaglandin analogue selected from the group consisting of
16S-methyl-6-oxo-PGE$_1$ methyl ester,
17S,20-dimethyl-6-oxo-PGE$_1$ methyl ester,
15S-methyl-6-oxo-PGE$_1$,
17S,20-dimethyl-13,14-dihydro-6-oxo-PGE$_1$ methyl ester,
17S,20-dimethyl-6-oxo-PGE$_1$ alcohol,
17S,20-dimethyl-6S-PGI$_1$ methyl ester,
17S,20-dimethyl-trans-Δ$^2$-6RS-PGI$_1$ methyl ester,
17S,20-dimethyl-6,9α-nitrilo-PGI$_1$ methyl ester,
2-decarboxy-2-glycoloyl-17S,20-dimethyl-6S-PGI$_1$,
2-decarboxy-2-glycoloyl-15-cyclopentyl-16,17,18,19,20-pentanor-6S-PGI$_1$
17S,20-dimethyl-6S-PGI$_1$ alcohol,
15-cyclopentyl-16,17,18,19,20-pentanor-6S-PGI$_1$ alcohol and
15-(3-propylcyclopentyl)-16,17,18,19,20-pentanor-6,9α-nitrilo-PGI$_1$ alcohol
or a cyclodextrin clathrate thereof, or a non-toxic salt of 15S-methyl-6-oxo-PGE$_1$.

2. A method according to claim 1 in which the amount of prostaglandin analogue administered is from 0.1 to 100 μg per kg by oral administration or from 0.01 to 10 μg per kg by parenteral administration.

3. A method according to claim 1 in which the amount of prostaglandin analogue administered is from 0.1 to 100 μg by oral administration or from 0.01 to 50 μg by parenteral administration.

4. A method according to claim 1 in which the amount of prostaglandin analogue administered is from 1 to 50 μg by oral administration or from 0.1 to 20 μg by parenteral administration.

5. A method according to claim 1 in which the cytodamage is associated with liver disease.

6. A method according to claim 1 in which the cytodamage is associated with pancreatic disease.

7. A method according to claim 1 in which a prostaglandin analogue selected from the group consisting of
16S-methyl-6-oxo-PGE$_1$ methyl ester,
17S,20-dimethyl-6-oxo-PGE$_1$ methyl ester,
17S,20-dimethyl-13,14-dihydro-6-oxo-PGE$_1$ methyl ester,
17S,20-dimethyl-6-oxo-PGE$_1$ alcohol,
17S,20-dimethyl-6S-PGI$_1$ methyl ester,
17S,20-dimethyl-trans-Δ$^2$-6RS-PGI$_1$ methyl ester,
17S,20-dimethyl-6,9α-nitrilo-PGI$_1$ methyl ester,
2-decarboxy-2-glycoloyl-17S,20-dimethyl-6S-PGI$_1$,
17S,20-dimethyl-6S-PGI$_1$ alcohol and
15-(3-propylcyclopentyl)-16,17,18,19,20-pentanor-6,9α-nitrilo-PGI$_1$ alcohol
or a cyclodextrin clathrate thereof, is administered.

8. A method according to claim 7 in which the prostaglandin analogue is 16S-methyl-6-oxo-PGE$_1$ methyl ester.

9. A method according to claim 7 in which the prostaglandin analogue is 17S,20-dimethyl-6-oxo-PGE$_1$ methyl ester.

10. A method according to claim 7 in which the prostaglandin analogue is 17S,20-dimethyl-13,14-dihydro-6-oxo-PGE$_1$ methyl ester.

11. A method according to claim 7 in which the prostaglandin analogue is 17S,20-dimethyl-6-oxo-PGE$_1$ alcohol.

12. A method according to claim 7 in which the prostaglandin analogue is 17S,20-dimethyl-6S-PGI$_1$ methyl ester.

13. A method according to claim 7 in which the prostaglandin analogue is 17S,20-dimethyl-trans-Δ$^2$-6RS-PGI$_1$ methyl ester.

14. A method according to claim 7 in which the prostaglandin analogue is 17S,20-dimethyl-6,9α-nitrilo-PGI$_1$ methyl ester.

15. A method according to claim 7 in which the prostaglandin analogue is 2-decarboxy-2-glycoloyl-17S,20-dimethyl-6S-PGI$_1$.

16. A method according to claim 7 in which the prostaglandin analogue is 17S,20-dimethyl-6S-PGI$_1$ alcohol.

17. A method according to claim 7 in which the prostaglandin analogue is 15-(3-propylcyclopentyl)-16,17,18,19,20-pentanor-6,9α-nitrilo-PGI$_1$ alcohol.

* * * * *